United Stat

Levy, Jr. et al.

[11] 4,074,368

[45] Feb. 21, 1978

[54] INTRAOCULAR LENS WITH HIGH MAGNIFICATION

[75] Inventors: Chauncey F. Levy, Jr., 1299 Portland Ave., Rochester, N.Y. 14621; Richard J. Pegis, Rochester, N.Y.

[73] Assignee: Said Chauncey F. Levy, Jr., by said Richard J. Pegis

[21] Appl. No.: 721,198

[22] Filed: Sept. 8, 1976

[51] Int. Cl.² .......................... A61F 1/16; A61F 1/24
[52] U.S. Cl. ........................................ 3/13; 350/211; 350/212
[58] Field of Search .................. 3/13, 1; 350/211, 212

[56] References Cited

U.S. PATENT DOCUMENTS

| 3,572,886 | 3/1971 | Cupertino et al. | 350/212 X |
| 3,673,616 | 7/1972 | Fedorov et al. | 3/13 |
| 4,010,496 | 3/1977 | Neefe | 3/13 |

OTHER PUBLICATIONS

"Artiphakia and Aniseikonia" by R. C. Troutman, American Journal of Ophthalmology, vol. 56, No. 2, Oct. 1963 pp. 602-639, 3-13.

Primary Examiner—Ronald L. Frinks
Attorney, Agent, or Firm—Hoffman Stone

[57] ABSTRACT

A sub-miniature optical system, based in principle on the Galilean telescope, for implantation in the eye following surgical removal of the natural lens. The system is made of methyl methacrylate and includes so-called air-lenses formed by bubbles defined by optically curved surfaces within the acrylic bodies. The positive element is surgically secured adjacent to the pupil. The negative element is mechanically connected to the positive element, and extends from it to within a few millimeters of the retina at the rear of the eye. The strength of the positive element is approximately 126 diopters for cases where the cornea is retained, and the strength of the negative element is about -2000 diopters, more or less, depending on its spacing from the positive element.

8 Claims, 2 Drawing Figures

INTRAOCULAR LENS WITH HIGH MAGNIFICATION

BRIEF DESCRIPTION

This invention relates to an intraocular lens system for implantation in the eye for relief of conditions such as macular degeneration and diabetic retinopathy.

Heretofore, people suffering from macular degeneration or diabetic retinopathy have been unable to read except through strong magnifying glasses which require the reading matter to be held very closely to the eye and provide a very severely restricted field of view.

The invention contemplates an optical system for implantation in the eye that will permit reading at normal distances, say about thirty centimeters, between the eye and the printed page, and provide a much larger field of view than heretofore possible with simple magnifiers.

The system of the invention makes use of gas filled bubbles in solid bodies of transparent plastic to achieve the refraction needed for focussing in the relatively short space available inside the eye. The system is, in optical engineering terms, a Galilean telescope. Its positive element consists of a body of methyl methacrylate having a bubble in it bounded by optically curved front and back surfaces, and may be described as either a biconcave air lens within a solid medium (positive power) or two biconvex plastic lenses in tandem. Because the refractive index of the aqueous humour is relatively close to the index of the acrylic material, and the front and rear surfaces, therefore, provide relatively little refraction, it is believed that the term air lens is more apt.

The negative element of the system is composed of a second cylinder of methyl methacrylate having one or more air lenses to provide the negative power required. The positive and negative elements are mechanically secured to each other, and the positive element is surgically secured in place near the pupil. The exit end of the negative element lies a few milllimeters in front of the retina.

The air lenses not only enable the achievement of adequate focussing in the short distance available, but also enable matching the specific gravity of the system to the specific gravity of the aqueous humour so that the system will have neutral buoyancy in the aqueous humour, or the salt solution that may be used to replace it and most of the vitreous humour, and not tend to pivot in response to gravity about its point of attachment near the pupil.

DETAILED DESCRIPTION

Figure 1:
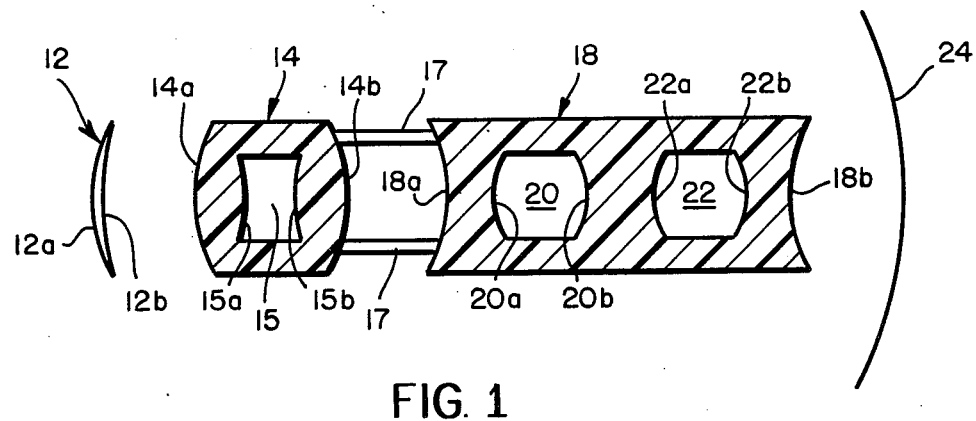
Figure 2:
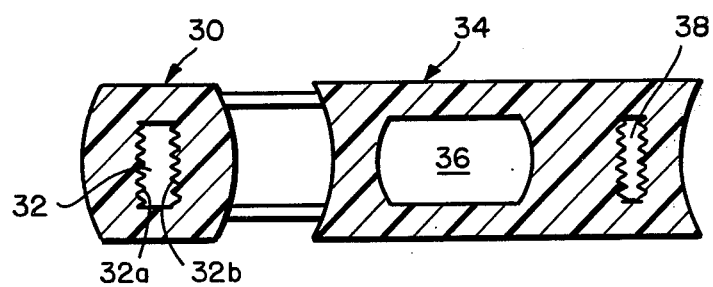

Representative embodiments of the invention will now be described in detail in conjunction with the accompanying drawing, wherein:

FIG. 1 is a longitudinal sectional view of an optical system according to the invention having smoothly curved optical surfaces; and FIG. 2 is a longitudinal sectional view of an optical system according to a modified form of the invention having optical surfaces of the micro-Fresnel type.

Referring now to FIG. 1, a lens system according to a first embodiment of the invention comprises a first element 14 having an optical power of about 126 diopters, more or less, depending on the dimensions of the eye for which it is intended. Also, if the patient's cornea has been damaged or is opacified, it is contemplated that the positive element will be extended through the cornea, and its power increased by about 38 to 48 diopters so that it will include the power normally provided by the cornea.

The front and rear surfaces 14a and 14b, respectively, of the element 14 are convex, and the element encloses a bubble 15 having front and rear surfaces 15a and 15b, respectively, that are also convex as seen from each other. The bubble 15, regarded in section, may be designated a biconcave air lens, and it is this air lens that provides most of the positive refractive power of the element because the outer convex surfaces 14a and 14b contact the aqueous humour when the lens is in place, and the refractive indices of the aqueous humour and methyl methacrylate are not very different from each other.

The element 14 is arranged to be secured to an element of the eye such as the iris by any desired means such as clips or simple sutures (not shown). Several different arrangements for securing intraocular lenses near the pupil are known, and the particular method of attachment is not a part of the present invention nor limiting to it.

The negative element 18 is mechanically fastened to the positive element 14 by any desired means that do not obstruct the path of light between the two elements. As shown, the attachment is by three angularly spaced methyl methacrylate pins 17, which may be cemented in receptor holes (not designated) in the respective elements 14 and 18. The two elements 14 and 18, taken together with the connecting means, constitute a body of a size and shape for implantation in the human eye.

A total power of about −2000 diopters is needed in the negative element 18, and to achieve this in the embodiment of FIG. 1, two air lenses 20 and 22, respectively, are arranged in tandem. Again, as with the positive element, the principal refractive surfaces are those facing the air in the bubbles 20 and 22, although in all cases the curvatures of the methacrylate-aqueous humour interfaces should be taken into account.

It will be recognized that with the relatively large number of refractive surfaces in the system, there can be found many different combinations of curvatures for the various surfaces and the spacings between them that will provide the desired overall power. Accordingly, the specific curvatures and spacings given in the following Table are illustrative only. They characterize an optical design based on an entrance pupil of 2 mm. diameter, and optimized in respect of geometrical image quality, taking into account also the curvature of the retina.

TABLE

LENS DESIGN

| Surface | Radius of Curvature, mm. | Distance to next rearward surface, mm. |
|---|---|---|
| Object (not shown) | plano | 300. |
| Front 12a of cornea | +7.9800 | 1.1500 |
| Rear 12b of cornea | +6.2200 | 1.9954 |
| Front 14a of pos. element | +8.9978 | 1.0000 |
| Front 15a of pos. bubble | −9.0023 | 0.5004 |
| Rear 15b of pos. bubble | +9.0015 | 1.0000 |
| Rear 14b of pos. element | −9.0023 | 3.3946 |
| Front 18a of neg. element | −2.2012 | 1.0004 |
| Front 20a of 1st bubble | +2.1981 | 2.0000 |
| Rear 20b of 1st bubble | −2.1915 | 0.9980 |
| Front 22a of 2nd bubble | +2.2055 | 2.0000 |
| Rear 22b of 2nd bubble | −2.0488 | 0.1284 |
| Rear 18b of neg. element | +9.3925 | 8.8317 |
| Retina 24 | −12.0000 | |

These specifications provide a field of view of about three centimeters diameter at the nominal object distance of about thirty centimeters, and a magnification of about five stated as the ratio between the height of the image formed by the lens system on the retina and the height of an image of the same object at the same distance formed on the retina of a normal eye.

According to a second embodiment of the invention the curves of the air lenses may be constituted by micro-Fresnel grooves and ridges as shown in FIG. 2. In this case, the system is designed to provide the same over-all focal length and magnification as in the smoothly curved embodiment shown in FIG. 1. The system as shown includes a positive element 30 having a bubble 32 with front and rear micro-Fresnel surfaces 32a and 32b, respectively, and a negative element 34 having a front bubble 36 and a rear bubble 38.

It is usually preferred in the design of tandem arrangements of Fresnel lenses to mount confronting lenses relatively close to each other, and if this is done in this modified form of the invention, the negative element 34 should include one pair of confronting Fresnel lenses constituting the front and rear surfaces, respectively, of the rear air lens 38, and providing the major part of the power of the negative element. The element 34 will then include, also, a forward air lens 36 having smoothly curved front and rear surfaces designed to correct aberration introduced by the Fresnel lenses. The size of the forward air lens 36 is selected to provide the desired neutral buoyancy.

In making the optical calculations, especially in regard to the spacing between the pairs of confronting optical surfaces that define the air lenses, account should be taken of the specific gravity of the methyl methacrylate relative to the specific gravity of the aqueous humour, or the artificial solution used to replace it and the vitreous humour. Methyl methacrylate is denser than the aqueous humour, and it is desired that the lens system, or, preferably, each of the elements 14 and 18, and 30 and 34 have an over-all density approximately the same as the aqueous humour, thereby neutralizing gravitational effects, which would otherwise tend to pivot the system downwardly about its attachment at the front of the eye.

What is claimed is:

1. An intraocular lens system comprising a body of a transparent material of a size and shape for implantation in the human eye and having front and rear surfaces, said body including a plurality of transparent bubbles completely enclosed therein and optically in tandem along the length thereof, the transverse internal surfaces of said body that define the front and rear boundaries of said bubbles being optically curved for refracting light passing lengthwise through said body and said bubbles between the front and rear surfaces of said body, the boundaries of a bubble adjacent to the front surface being curved for positive refraction of light and the boundaries of a bubble adjacent to the rear surface being curved for negative refraction.

2. An intraocular lens system comprising a body of a transparent material of a size and shape for implantation in the human eye and having front and rear surfaces, said body including two transparent bubbles completely enclosed therein and optically in tandem along the length thereof, the transverse internal surfaces of said body that define the front and rear boundaries of said bubbles being optically curved for refracting light passing lengthwise through said body and said bubbles between the front and rear surfaces of said body, the boundaries of the bubble adjacent to the front surface being curved for positive refraction of light and the boundaries of the bubble adjacent to the rear surface being curved for negative refraction.

3. An intraocular lens system according to claim 1 wherein said body includes two longitudinally spaced major portions, and angular spaced connecting portions extending between said major portions, said bubbles lying in said major portions.

4. An intraocular lens system according to claim 1 including two bubbles adjacent to the rear surface both having their boundaries curved for negative refraction.

5. An intraocular lens system according to claim 4 wherein the boundaries of the rear one of the two bubbles adjacent to the rear surface of said body are shaped as micro-Fresnel lenses, and the boundaries of the forward one of said two bubbles adjacent to the rear surface are smoothly curved.

6. An intraocular lens system according to claim 1 wherein said transverse internal surfaces are smoothly curved.

7. An intraocular lens system according to claim 1 wherein selected ones of said transverse internal surfaces are shaped as micro-Fresnel lenses.

8. An intraocular lens system according to claim 1 wherein at least one of said transverse internal surfaces is shaped as a micro-Fresnel lens.

* * * * *